(12) United States Patent
Oakley

(10) Patent No.: US 7,247,773 B2
(45) Date of Patent: Jul. 24, 2007

(54) HAMMER COTTON CULTIVAR PLANT AND SEED

(75) Inventor: Stephen R. Oakley, Bakersfield, CA (US)

(73) Assignee: Bayer CropScience GmbH (DE)

( * ) Notice: Subject to any disclaimer, the term of this patent is extended or adjusted under 35 U.S.C. 154(b) by 0 days.

(21) Appl. No.: 11/196,858

(22) Filed: Aug. 4, 2005

(65) Prior Publication Data

US 2005/0257296 A1 Nov. 17, 2005

Related U.S. Application Data

(60) Provisional application No. 60/653,007, filed on Feb. 15, 2005.

(51) Int. Cl.
*A01H 5/00* (2006.01)
*A01H 5/10* (2006.01)
*A01H 4/00* (2006.01)
*A01H 1/00* (2006.01)
*C12N 15/82* (2006.01)

(52) U.S. Cl. ............. 800/314; 800/260; 800/265; 800/279; 800/298; 800/300; 800/301; 800/302; 435/410

(58) Field of Classification Search ........... 800/260, 800/265, 279, 298, 300, 301, 302, 314; 435/410
See application file for complete search history.

(56) References Cited

U.S. PATENT DOCUMENTS

| | | | | |
|---|---|---|---|---|
| 5,304,719 | A | * | 4/1994 | Segebart .............. 800/303 |
| 5,367,109 | A | * | 11/1994 | Segebart ............ 800/320.1 |
| 5,516,979 | A | | 5/1996 | Tal |
| 5,521,078 | A | | 5/1996 | John |
| 5,523,520 | A | | 6/1996 | Hunsperger et al. |
| 5,583,036 | A | | 12/1996 | Rangan et al. |
| 5,608,142 | A | | 3/1997 | Barton et al. |
| 5,608,148 | A | | 3/1997 | John |
| 5,695,999 | A | | 12/1997 | Rangan et al. |
| 5,763,755 | A | * | 6/1998 | Carlone ............. 800/320.1 |
| 5,846,797 | A | | 12/1998 | Strickland |
| 5,850,009 | A | * | 12/1998 | Kevern ................ 800/271 |
| 5,869,720 | A | | 2/1999 | John |
| 5,885,963 | A | | 3/1999 | Stockhoff et al. |
| 5,932,713 | A | | 8/1999 | Kasukabe et al. |
| 5,986,181 | A | | 11/1999 | Trolinder et al. |
| 6,008,438 | A | * | 12/1999 | Keim ................... 800/314 |
| 6,040,504 | A | | 3/2000 | Rice et al. |
| 6,166,294 | A | | 12/2000 | Kasukabe et al. |
| 6,169,174 | B1 | | 1/2001 | Hasegawa et al. |
| 6,200,561 | B1 | | 3/2001 | Bilimoria |
| 6,242,257 | B1 | | 6/2001 | Tuli et al. |
| 6,259,003 | B1 | | 7/2001 | Fujisawa et al. |
| 6,329,570 | B1 | | 12/2001 | Martineau |
| 6,472,588 | B1 | | 10/2002 | Haigler et al. |
| 6,541,448 | B2 | | 4/2003 | Isaac et al. |
| 6,566,586 | B1 | | 5/2003 | Stalker et al. |
| 6,573,437 | B1 | | 6/2003 | Anderson et al. |
| 6,610,907 | B1 | | 8/2003 | Zhu et al. |
| 6,620,990 | B1 | | 9/2003 | Rangan et al. |
| 6,624,344 | B1 | | 9/2003 | Rangan et al. |
| 6,660,914 | B1 | | 12/2003 | Rangan et al. |
| 6,710,228 | B1 | | 3/2004 | Yenofsky et al. |
| 6,730,824 | B2 | | 5/2004 | Petolino et al. |
| 6,818,807 | B2 | | 11/2004 | Trolinder et al. |
| 6,858,777 | B2 | | 2/2005 | Zhong et al. |
| 6,893,826 | B1 | | 5/2005 | Hillyard et al. |
| 2001/0026939 | A1 | | 10/2001 | Rice et al. |
| 2002/0049999 | A1 | | 4/2002 | Allen et al. |
| 2002/0066121 | A1 | | 5/2002 | Kosegi et al. |
| 2002/0187538 | A1 | | 12/2002 | Essenberg et al. |
| 2003/0024005 | A1 | | 1/2003 | Hillyard et al. |
| 2003/0024015 | A1 | | 1/2003 | Davis |
| 2003/0074697 | A1 | | 4/2003 | Allen et al. |
| 2003/0097687 | A1 | | 5/2003 | Trolinder et al. |
| 2003/0106089 | A1 | | 6/2003 | McBride et al. |
| 2003/0143744 | A1 | | 7/2003 | Dunwell et al. |
| 2003/0154516 | A1 | | 8/2003 | Rathore et al. |
| 2003/0204866 | A1 | | 10/2003 | Davis |
| 2003/0221218 | A1 | | 11/2003 | Wilkins |
| 2004/0009504 | A1 | | 1/2004 | Rangwala et al. |
| 2004/0009601 | A1 | | 1/2004 | Wilkins et al. |
| 2004/0016019 | A1 | | 1/2004 | Yenofsky et al. |
| 2004/0045054 | A1 | | 3/2004 | Beazley et al. |
| 2004/0087030 | A1 | | 5/2004 | Armstrong et al. |
| 2005/0005334 | A1 | | 1/2005 | Trolinder et al. |

OTHER PUBLICATIONS

Poehlman, J.M. and D.A. Sleper. 1995. Breeding Field Crops. 4th ed. Iowa State University Press, Ames, Iowa, p. 473.*
Dow AgroSciences, Risk assessment and risk management plant, DIR 040/2003, Nov. 2003, p. 25, paragraph 115.*
Yuval Eshed et al, *Less-Than-Additive Epistatic Interactions of Quantitative Trait Loci in Tomato*, Genetics, Aug. 1996, vol. 143, No. 4, Published Monthly by the Genetics Society of America.
Walter R. Fehr et al., Principles of Cultivar Development, Theory and Technique, Genetic Principles, *Symbolism For Describing Inbred Lines*, vol. 1, Macmillan Publishing Company.
Frish et al, *Minimum Sample Size and Optimal Positioning of Flanking Markers in Marker-Assisted Backcrossing for Transfer of a Target Gene*, Crop Science, Jul.-Aug. 1999, vol. 39, No. 4, pp. 967-975.

(Continued)

*Primary Examiner*—David H. Kruse
*Assistant Examiner*—Keith O. Robinson
(74) *Attorney, Agent, or Firm*—Patterson, Thuente, Skaar & Christensen, P.A.

(57) ABSTRACT

A cotton cultivar designated HAMMER is disclosed. The invention relates to the seeds of cotton cultivar HAMMER, to the plants and plant parts of cotton HAMMER and to methods for producing a cotton plant produced by crossing the cultivar HAMMER with itself or another cotton variety. The invention further relates to hybrid cotton seeds and plants produced by crossing the cultivar HAMMER with itself or with another cotton cultivar.

23 Claims, No Drawings

OTHER PUBLICATIONS

Frish et al., *Comparison of Selection Strategies for Marker-Assisted Backcrossing of a Gene*, Crop Science, Sep.-Oct. 1999, vol. 39, No. 5, pp. 1295-1301.

Anoymous, *The Biology and Ecology of Cotton (Gossypium hirsutum) in Australia*, Office of the Gene Technology Regulator, Aug. 2002, pp. 1-30.

Frederic Hospital, *Marker-Assisted Backcross Breeding: A Case-Study in Genotype Building Theory*.

Frederic Hospital, *Selection in Backcross Programmes*, Philosophical Transactions of The Royal Society, No. 360, pp. 1503-1511, 2005.

T. Kraft et al., *Linkage Disequilibrium and Fingerprinting in Sugar Beet*, Theoretical and Applied Genetics, vol. 101, Nos. 1-2, pp. 323-326, Jul. 2000.

Rajiv Mishra et al., *Development of a Highly Regenerable Elite Acala Cotton (Gossypium Hirsutum cv. Maxxa)—A Step Towards Genotype-Independent Regeneration*, Plant Cell, Tissue and Organ Culture, An International Journal On Biotechnology of Higher Plants, No. 73, pp. 21-35, 2003, Kluwer Academic Publishers.

J. Hillel, *DNA Fingerprints Applied to Gene Introgression in Breeding Programs*, GENETICS, vol. 124, pp. 783-789, Jan.-Apr. 1990.

Peter M. Visscher et al., *Marker-Assisted Introgression in Backcross Breeding Programs*, Genetics, vol. 144, pp. 1923-1932, Nov. 1996.

Wilson, *Yield, Earliness, and Fiber Properties of Cotton Carrying Combined Traits for Pink Bollworm Resistance*, Crop Science, vol. 29, No. 1, Jan.-Feb. 1989, pp. 7-12.

\* cited by examiner

HAMMER COTTON CULTIVAR PLANT AND SEED

CROSS-REFERENCES TO RELATED APPLICATION

This application claims the benefit of U.S. Provisional Application 60/653,007, filed Feb. 15, 2005, which is incorporated herein in its entirety by reference.

BACKGROUND OF THE INVENTION

The present invention relates to an Acala cotton (*Gossypium hirsutum* L.) seed, a cotton plant and plant parts, a cotton variety and a cotton hybrid. This invention further relates to a method for producing cotton seed and plants.

Cotton is the world's leading natural fiber and the second largest oilseed crop. Cotton production is a multi-billion dollar industry, and therefore a vital agricultural commodity to both the U.S. and global economies. In addition to textile manufacturing, cotton and cotton by-products provide raw materials that are used to produce a wealth of consumer-based products such as foodstuffs, livestock feed, fertilizer, and paper.

Enhancing the ability of cotton varieties to provide higher and more economically achieved yields and commercial qualities of fiber and oil involves enhancing the genetic potential for these complexly inherited traits. Additionally, constantly evolving diseases, insects, and environmental stresses continually threaten previously resistant and tolerant varieties. To this end, improving cotton varieties is a challenging and ongoing undertaking.

SUMMARY OF THE INVENTION

The present invention relates to a cotton seed, a cotton plant and plant parts, a cotton variety and a method for producing a cotton plant.

The present invention further relates to a method of producing cotton seeds and plants by crossing a plant of the instant invention with another cotton plant.

This invention further relates to the seeds of cotton variety HAMMER, to the plants of cotton variety HAMMER and to methods for producing a cotton plant produced by crossing the cotton variety HAMMER with itself or another cotton line. Thus, any such methods using the cotton variety HAMMER are part of this invention including: selfing, backcrosses, hybrid production, crosses to populations, and the like.

In another aspect, the present invention provides for single trait converted plants of HAMMER. The single transferred trait may preferably be a dominant or recessive allele. Preferably, the single transferred trait will confer such traits as herbicide resistance, insect resistance, resistance for bacterial, fungal, or viral disease, male fertility, male sterility, enhanced fiber quality, and industrial usage. The single trait may be a naturally occurring cotton gene or a transgene introduced through genetic engineering techniques.

In yet another aspect, the present invention provides a method of introducing a desired trait into cotton cultivar HAMMER wherein the method comprises crossing a HAMMER plant with a plant of another cotton cultivar that comprises a desired trait to produce $F_1$ progeny plants, wherein the desired trait is selected from the group consisting of male sterility, herbicide resistance, insect resistance, and resistance to bacterial disease, fungal disease or viral disease; selecting progeny plants that have the desired trait to produce selected progeny plants; crossing the selected progeny plants with the HAMMER plants to produce backcross progeny plants; selecting for backcross progeny plants that have the desired trait and physiological and morphological characteristics of cotton cultivar HAMMER to produce selected backcross progeny plants; and repeating these steps to produce selected first or higher backcross progeny plants that comprise the desired trait and all of the physiological and morphological characteristics of cotton cultivar HAMMER as determined at the 5% significance level when grown in the same environmental conditions. Included in this aspect of the invention is the plant produced by the method wherein the plant has the desired traits and all of the physiological and morphological characteristics of cotton cultivar HAMMER as determined at the 5% significance level when grown in the same environmental conditions.

In still yet another aspect, the present invention provides regenerable cells for use in tissue culture of cotton plant HAMMER. The tissue culture will preferably be capable of regenerating plants having the physiological and morphological characteristics of the foregoing cotton plant, and of regenerating plants having substantially the same genotype as the foregoing cotton plant. Preferably, the regenerable cells in such tissue cultures will be embryos, protoplasts, meristematic cells, callus, pollen, leaves, anthers, roots, root tips, flowers, seeds, or stems. Still further, the present invention provides cotton plants regenerated from the tissue cultures of the invention.

DETAILED DESCRIPTION

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. Additionally, the materials, methods, and examples are illustrative only and not intended to be limiting.

Cotton

In tropical areas cotton is a perennial shrub. However, cotton is grown commercially as an annual.

Following germination, plant growth continues with the development of a central, main stem bearing the first true leaves spirally, along its axis. Leaves are typically 10–15 centimeters wide, palmately-lobed, with 3–5 lobes on each leaf. The main stem initially branches from axillary buds from the main stem leaves. Either vegetative (monopodial) or fruiting (sympodial) branches are produced. Both branch types bear true leaves; however, about 5–6 weeks after planting the total area of leaves borne on fruiting branches exceeds that of the main stem and vegetative branches. During growth and development, the plant canopy is said to begin to "close." Early canopy closure may be agronomically desirable, because the resulting shading may limit weed growth and decrease moisture evaporation from the underlying topsoil. Reproductive maturity begins with the formation of floral buds termed "squares." Typically, about 25 days elapse between the onset of a square and anthesis (flower opening). Under normal crop conditions, about 60% of squares and immature fruit abscise prematurely. Cotton flowers usually anthese at, or near, dawn and remain open for a single day. At anthesis, the pettles are creamy-white, turning pink-red within about one day of pollination, after which they abscise. Soon after anthesis, the anthers of cotton flowers dehisce, thereby discharging their pollen. Cotton pollen is relatively large and heavy and, thus, is not easily dispersed by wind. To this end, cotton is a facultative self-pollinator but out-crosses when insect pollinators are present. Cotton pollen remains viable for about 12 hours. Fertilization of ovules occurs about 12–30 hours after pollination.

When the ovules in these inflorescences are fertilized, they develop into capsules called "bolls". Seeds and fiber are borne in the bolls. The fibers of cotton—commercially termed lint and botanically designated trichomes—originate as epidermal hairs growing from the surface of the fertilized ovule. These fibers first elongate, then thicken as they mature. As they develop, the bolls are initially spherical to ovoid and are pale green. Maximum boll size occurs about 25 days after fertilization. Full maturity occurs approximately 20 days thereafter. Mature bolls are thick and leathery, drying rapidly to become brittle and brown. At maturity the bolls split open to expose the seeds and associated fibers.

During harvest, the lint and seeds of cotton varieties are mechanically or manually separated from the opened bolls in the field. The lint is then separated from the seeds by ginning and compressed into bales for transport and storage.

The ginned seed is covered by short, fuzzy fibers known as linters. The linters are usually removed before the seed can be used for planting or crushed for oil extraction. During removal linters are removed from the seeds and first and second cuts. First-cut linters have the longest fiber lengths and are used in mattresses, furniture upholstery and mops. Second-cut linters represent a source of cellulose for chemical and food uses. Food uses include high fiber dietary products and viscosity enhancers (thickeners) for products such as ice cream, salad dressings and toothpaste. Chemical uses comprise cellulose derivatives such as cellulose acetate and nitrocellulose. The delinted cotton seed can be processed to produce oil, meal, and hulls. Cotton seed oil has been long used in foods and other products, such as edible vegetable oil, margarine, soap, and plastics. Cotton seed or meal, flour, and hulls are also used in food products and animal feeds. However, the presence of natural toxicants (gossypol and cyclopropenoid fatty acids) in the seeds limits usage in non-ruminants.

Plant Breeding

Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. In cotton, the important traits include higher fiber (lint) yield, earlier maturity, improved fiber quality, resistance or tolerance to diseases, insects, drought, heat, and improved agronomic traits.

Pureline cultivars of cotton are commonly bred by hybridizing two or more parents followed by selection in subsequent segregating generations. The complexity of inheritance, specific breeding objectives, and available resources influence the actual breeding methods employed. Pedigree breeding, recurrent selection breeding and backcross breeding are breeding methods commonly used in self-pollinated crops such as cotton. These methods refer to the manner in which breeding pools or populations are made in order to combine desirable traits from two or more cultivars or various broad-based sources. The procedures commonly used for selection of desirable individuals or populations of individuals are mass selection, plant-to-row selection and single seed descent or modified single seed descent. One, or a combination of these selection methods, can be used in the development of a cultivar from a breeding population.

Pedigree breeding is primarily used to combine favorable genes into a totally new cultivar that is different in many traits than either parent used in the original cross. It is commonly used for the improvement of self-pollinating crops. Two parents with desired traits are crossed to produce an $F_1$ (filial generation 1) population. Another parent may be then crossed to the $F_1$ hybrid. An $F_2$ population is produced by selfing the $F_1$ plants from the initial mating(s). Selection of desirable individual plants may begin as early as the $F_2$ generation in maximum gene segregation occurs. Individual plant selection can occur for one or more generations. Successively, seed from each selected plant can be planted in individually identified rows, known as progeny rows, to evaluate the line and to increase the seed quantity of that line or to further select individual plants. Once a progeny row is selected as having desirable traits, the row and seed from the row becomes what is known as an advanced line that is specifically identifiable from other advanced lines obtained from the same original population. At an advanced generation (i.e., $F_5$ or higher) seed of individual lines are evaluated in replicated testing. The best lines or a mixture of phenotypically similar lines from the same original cross are tested for potential release as new cultivars.

Descriptions of other breeding methods that are commonly used for different traits and crops can be found in one of several references, e.g., A. R. Hallauer and J. B. Miranda Fo, Quantitative Genetics in Maize Breeding, Iowa State University Press, Ames, Iowa (1981); G. Namkoong, Introduction to Quantitative Genetics in Forestry, U.S. Dept. Agric. Forest Service Tech. Bull. Number 1588 (1979); F. N. Briggs and P. F. Knowles, Introduction to Plant Breeding, Reinhold Publishing Company, New York (1967), R. W. Allard, Principles of Plant Breeding, Wiley and Sons, New York (1960), N. W. Simmonds, Principles of Crop Improvement, Longman Group, Ltd., London (1979); J. M. Poehlman, Breeding Field Crops, 2d Ed., AVI Publishing Co., Inc. Westport, Conn. (1979), and Cotton, R. J. Kohel and C. F. Lewis Editors, American Society of Agronomy & Crop Science Society of America, Madison, Wis., U.S.A. (1984).

The single seed descent procedure usually refers to cyclically planting a segregating population, harvesting one seed from every plant, and combining these seeds into a bulk which is then planted to form the next generation. When the population has been advanced to the desired level of inbreeding, the plants from which lines are derived will each trace to different $F_2$ individuals. The primary advantages of single seed descent procedures are to delay selection until a high level of homozygosity (e.g., lack of gene segregation) is achieved in individual plants, and to move through these early generations quickly, e.g., via winter nurseries.

The modified single seed descent procedure includes harvesting multiple seeds (e.g., a single locket or boll) from each plant in a population, then combining the harvested seeds to form a bulk. Part of the bulk is used to plant the next generation and part is put in reserve. This procedure has been used to save labor at harvest and to maintain adequate seed quantities of the population.

Selection for desirable traits can occur at any segregating generation ($F_2$ and beyond). Selection pressure is exerted on a population by growing the population in an environment where the desired trait is maximally expressed, to thereby identify individuals or lines possessing desired expressions of the trait. For instance, selection can occur for disease resistance when the plants or lines are inoculated with disease pathogen. In this situation, the breeder selects only those individuals or lines with little or no disease symptoms. The selected individuals are assumed to be resistant.

Promising advanced lines are thoroughly tested and compared to popular cultivars ("checks") in environments representative of the commercial target area(s) for a number of growing seasons, e.g., three or more. The best advanced lines exhibiting superior performances over the checks are candidates to become new commercial cultivars. Those lines still deficient in a few traits are discarded or utilized as parents to produce new populations for further selection.

These processes, lead to the final step of marketing and distribution and usually take from seven to twelve years from the time the initial breeding cross is made. Therefore, development of new cultivars is a time-consuming process that requires precise forward planning, efficient use of resources, and scientists with the experience and skill to visually select superior individuals and the expertise to manage and evaluate more technical selection tools (e.g., evaluation of statistical data from performance trials).

The most difficult task in breeding programs is identification of genetically superior individuals, because for most traits the true genotypic value is masked by other confounding plant traits or environmental factors. One method of identifying a superior plant is to observe its performance relative to other experimental lines and widely grown standard cultivars over several environments. For many, often quantitatively inherited traits, a single observation is inconclusive and replicated observations over time and space are required to provide a good estimate of a line's genetic worth.

As stated above, the goal of a commercial cotton breeding program is to develop new, unique and superior cotton cultivars. The breeder initially selects and crosses two or more parental lines followed by selection in segregating generations, thus producing many new genetic combinations. While the breeder can theoretically generate billions of different genetic combinations via this procedure, the breeder has no direct control over which genetic combinations will actually arise. Therefore, two breeders evaluating segregating populations arising from the same parents will never develop the same line having the same traits.

Each year, the plant breeder selects the germplasm to advance to the next generation. This germplasm is grown under unique and differing geographical, climatic and soil conditions. Further selections are then made during and at the end of the growing season. The lines which are developed are unpredictable in the combinations and expressions of traits present therein. This unpredictability is, inter alia, because selection occurs in unique environments, with no control at the molecular level (using conventional breeding procedures), and with millions of different possible genetic combinations being generated. Thus, a breeder of ordinary skill in the art cannot predict the final resulting lines developed, except possibly in a very gross and general fashion. The same breeder cannot produce, with any reasonable likelihood, the same cultivar twice by using the exact same original parents and the same selection techniques. Because of this lack of predictable success, rather than relying a given cross, a breeder, in any given year, makes several crosses using several parental combinations to achieve the same or differing breeding objectives. This unpredictability additionally necessitates expending large amounts of research resources to develop superior new cotton cultivars.

Proper testing should detect any major faults and establish the level of superiority or improvement over current cultivars. In addition to showing superior performance, there must be a demand for a new cultivar that is compatible with industry standards or which creates a new market. The introduction of a new cultivar will thusly cause additional costs to the seed producer, grower, processor and consumer in terms of the special advertising, marketing and commercial production practices and new product utilization necessary to commercially realize the value of the new variety.

Cotton is an important and valuable field crop. Thus, a continuing goal of cotton plant breeders is to develop stable, high yielding cotton cultivars with superior combinations of economically desirable traits. The reasons for this goal are to maximize the amount and quality of the fiber produced on the land used, thus providing fiber, oil and food for animals and humans.

The cotton flower is monoecious in that the male and female structures are in the same flower. The crossed or hybrid seed is produced by manual crosses between selected parents. Floral buds of the parent used as the female are emasculated prior to the opening of the flower by manually removing the male anthers. At flowering, pollen from flowers of the parent plants designated as the male, are manually deposited on the stigmas of the previously emasculated flower. Seed developed from the cross is known as first generation ($F_1$) hybrid seed. Planting this seed produces $F_1$ hybrid plants, of which half their genetic component is from the female parent and half from the male parent. Segregation of genes begins at meiosis thus producing second generation ($F_2$) seed. Assuming multiple genetic differences between the original parents, each $F_2$ seed has a unique combination of genes.

This invention is also directed to methods for producing a cotton plant by crossing a first parent cotton plant with a second parent cotton plant, wherein the first or second cotton plant is the cotton plant from the cultivar HAMMER. Further, both the first and second parent cotton plants may be the cultivar HAMMER (e.g., self-pollination). Therefore, any methods using the cultivar HAMMER are part of this invention: selfing, backcrosses, hybrid breeding, and crosses to populations. Any plants produced using cultivar HAMMER as a parent are within the scope of this invention. As used herein, the term "plant" includes plant cells, plant protoplasts, plant cells of tissue culture from which cotton plants can be regenerated, plant calli, plant clumps, and plant cells that are intact in plants or parts of plants, such as pollen, flowers, embryos, ovules, seeds, pods, leaves, stems, roots, anthers and the like. Thus, another aspect of this invention is to provide for cells which upon growth and differentiation produce a cultivar having essentially all of the physiological and morphological characteristics of HAMMER.

Culture for expressing desired structural genes and cultured cells are known in the art. As is also known in the art, cotton is transformable and regenerable such that whole plants containing and expressing desired genes under regulatory control may be obtained. General descriptions of plant expression vectors, reporter genes, and transformation protocols can be found in Gruber, et al., "Vectors for Plant Transformation, in Methods in Plant Molecular Biology & Biotechnology" in Glich, et al., (Eds. pp. 89–119, CRC Press, 1993) and U.S. Pat. No. 6,620,990. Moreover GUS expression vectors and GUS gene cassettes are available from Clone Tech Laboratories, Inc., Palo Alto, Calif. while luciferase expression vectors and luciferase gene cassettes are available from Pro Mega Corp. (Madison, Wis.). General methods of culturing plant tissues are provided, for example, by Maki, et al., "Procedures for Introducing Foreign DNA into Plants" in Methods in Plant Molecular Biology & Biotechnology, Glich, et al., (Eds. pp. 67–88 CRC Press, 1993), U.S. Patent App. No. 2004/0009601, U.S. Pat. No. 6,620,990, and by Phillips, et al., "Cell-Tissue Culture and In-Vitro Manipulation" in Corn & Corn Improvement, 3rd Edition; Sprague, et al., (Eds. pp. 345–387) American Society of Agronomy Inc., 1988 and U.S. Pat. No. 5,244,802. Methods of introducing expression vectors into plant tissue include the direct infection or co-cultivation of plant cells with *Agrobacterium tumefaciens*, Horsch et al., Science, 227:1229 (1985), U.S. Patent App. No. 2004/0009601, and U.S. Pat. No. 6,620,990. Descriptions of *Agrobacterium* vectors systems and methods for *Agrobacterium*-mediated gene transfer are provided by Gruber, et al., supra.

Useful methods include but are not limited to expression vectors introduced into plant tissues using a direct gene transfer method such as microprojectile-mediated delivery, DNA injection, electroporation, transfection and the like. More preferably expression vectors are introduced into plant tissues using microprojectile-mediated delivery with a biolistic device or with *Agrobacterium*-mediated transformation. Transformant plants obtained with the protoplasm of the invention are intended to be within the scope of this invention.

The present invention contemplates a cotton plant regenerated from a tissue culture of a variety (e.g., HAMMER) or hybrid plant of the present invention. As is well known in the art, tissue culture of cotton can be used for the in vitro regeneration of a cotton plant. Tissue culture of various tissues of cotton and regeneration of plants therefrom is well known and widely published.

When the term cotton plant is used in the context of the present invention, this also includes any single trait conversions of that variety. The term single trait converted plant as used herein refers to those cotton plants which are developed by a plant breeding technique called backcrossing or via genetic engineering wherein essentially all of the desired morphological and physiological characteristics of a variety are recovered in addition to the single trait transferred into the variety. Backcrossing methods can be used with the present invention to improve or introduce a characteristic into the variety. The term backcrossing as used herein refers to the repeated crossing of a hybrid progeny back to the recurrent parent. The parental cotton plant which contributes the trait for the desired characteristic is termed the nonrecurrent or donor parent. This terminology refers to the fact that the nonrecurrent parent is used one time in the backcross protocol and therefore does not recur. The parental cotton plant to which the trait or traits from the nonrecurrent parent are transferred is known as the recurrent parent as it is used for several rounds in the backcrossing protocol (Poehlman & Sleper, 1994; Fehr, 1987). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a cotton plant is obtained wherein essentially all of the desired morphological and physiological characteristics of the recurrent parent are recovered in the converted plant, in addition to the single transferred gene from the nonrecurrent parent.

Alternatively, marker assisted backcrossing usually requires utilizing mapped molecular markers (e.g., SSRs) to screen the recurrent and nonrecurrent parents and the BC1, BC2, and BC2S1 (selfed BC1) generation, wherein a sufficient amount, e.g., about 200, of markers are used to screen the parents, often a fewer number, e.g., about 100, of markers are used to screen 100 to 150 BC1 individuals, and often still fewer, e.g., about 20, markers are used to screen about 100 BC2 individuals, and yet fewer still, e.g., about 2–5, markers are used to screen about 100 BC2S1 individuals. The desired essentially derived individuals or an individual, with the exception of the introduced allele, possessing essentially all the physiological and morphological characteristics will result from two backcrossing cycles and a single selfing cycle. The theory and protocols for marker assisted backcrossing are presented in Frisch et al., 1999, Minimum sample size and optimal positioning of flanking markers in marker-assisted backcrossing for transfer of a target gene, Crop Science 39: 967–975; Hillel et al., 1990, DNA fingerprint applied to gene introgression breeding programs, Genetics 124: 783–789; Visscher et al., 1996, Marker-assisted introgression in backcross breeding programs, Genetics 144: 1923–1932; and Frisch et al., 1999, Comparison of selection strategies for marker-assisted backcrossing of a gene, Crop Science 39:1295–1301.

The selection of a suitable recurrent parent is an important step for a successful backcrossing procedure. The goal of a backcross protocol is to alter or substitute a single trait or characteristic in the original variety. To accomplish this, a gene or genes of the recurrent variety are modified or substituted with the desired gene(s) from the nonrecurrent parent while retaining essentially all of the rest of the desired genetic, and therefore the desired physiological and morphological constitution of the original variety. The choice of the particular nonrecurrent parent will depend on the purpose of the backcross; one of the major purposes is to add some commercially desirable and/or agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many traits have been identified that are not regularly selected for in the development of a new variety but that can be improved by backcrossing techniques. Traits may or may not be transgenic; examples of these traits include, but are not limited to, cytoplasmic or nuclear male sterility, herbicide resistance, resistance for bacterial, fungal, or viral disease, insect resistance, male fertility, enhanced fiber quality, industrial usage, yield stability and yield enhancement. These traits are generally inherited through the nucleus.

Transformation

With the advent of molecular biological techniques allowing the isolation and characterization of genes that encode specific protein products, scientists in the field of plant biology developed a strong interest in engineering the genome of plants to contain and express foreign genes, or additional or modified versions of native, or endogenous, genes (perhaps driven by different promoters) in order to alter the traits of a plant in a specific manner. Such foreign additional and/or modified genes are referred to herein collectively as "transgenes". Over the last fifteen to twenty years several methods for producing transgenic plants have been developed, and the present invention in particular embodiments also relates to transformed versions of the claimed variety or line.

Plant transformation involves the construction of an expression vector that will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid and can be used alone or in combination with other plasmids to provide transformed cotton plants using transformation methods as described below to incorporate transgenes into the genetic material of the cotton plant(s).

Expression Vectors for Cotton Transformation: Marker Genes—Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene, which, when under the control of plant regulatory signals, confers resistance to kanamycin. Fraley et al., Proc. Natl. Acad. Sci. U.S.A., 80:4803 (1983). Another commonly used selectable marker gene is the hygromycin phosphotransferase gene which confers resistance to the antibiotic hygromycin. Vanden Elzen et al., Plant Mol. Biol., 5:299 (1985).

Additional selectable marker genes of bacterial origin that confer resistance to antibiotics include gentamycin acetyl transferase, streptomycin phosphotransferase and aminoglycoside-3'-adenyl transferase, the bleomycin resistance determinant. Hayford et al., Plant Physiol. 86:1216 (1988), Jones et al., Mol. Gen. Genet., 210:86 (1987), Svab et al., Plant Mol. Biol. 14:197 (1990) Hille et al., Plant Mol. Biol. 7:171 (1986). Other selectable marker genes confer resistance to herbicides such as glyphosate, glufosinate or bromoxynil. Comai et al., Nature 317:741–744 (1985), Gordon-Kamm et al., Plant Cell 2:603–618 (1990) and Stalker et al., Science 242:419–423 (1988).

Selectable marker genes for plant transformation that are not of bacterial origin include, for example, mouse dihydrofolate reductase, plant 5-enol-pyruvyl-shikimate-3-phosphate synthase (EPSP) and plant acetolactate synthase. Eichholtz et al., Somatic Cell Mol. Genet. 13:67 (1987), Shah et al., Science 233:478 (1986), Charest et al., Plant Cell Rep. 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include beta-glucuronidase (GUS), beta-galactosidase, luciferase and chloramphenicol acetyltransferase. Jefferson, R. A., Plant Mol. Biol. Rep. 5:387 (1987), Teeri et al., EMBO J. 8:343 (1989), Koncz et al., Proc. Natl. Acad. Sci. U.S.A. 84:131 (1987), DeBlock et al., EMBO J. 3:1681 (1984).

In vivo methods for visualizing GUS activity that do not require destruction of plant tissue are available. Molecular Probes publication 2908, Imagene Green™, p. 1–4 (1993) and Naleway et al., J. Cell Biol. 115:151a (1991). However, these in vivo methods for visualizing GUS activity have not proven useful for recovery of transformed cells because of low sensitivity, high fluorescent backgrounds and limitations associated with the use of luciferase genes as selectable markers.

A gene encoding Green Fluorescent Protein (GFP) has been utilized as a marker for gene expression in prokaryotic and eukaryotic cells. Chalfie et al., Science 263:802 (1994). GFP and mutants of GFP may be used as screenable markers.

Promoters

Genes included in expression vectors must be driven by nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions, the presence of light, interactions with chemical substances or contact with other organisms including, but not limited to, certain pathogens. Tissue-specific, tissue-preferred, cell type specific, and inducible promoters constitute the class of "non-constitutive" promoters. A "constitutive" promoter is a promoter which is active under most environmental conditions.

Inducible Promoters

An inducible promoter is operably linked to a gene for expression in cotton. Optionally, the inducible promoter is operably linked to a nucleotide sequence encoding a signal sequence which is operably linked to a gene for expression in cotton. With an inducible promoter the rate of transcription increases in response to an inducing agent.

Any inducible promoter operable in plants can be used in the instant invention. See Ward et al., Plant Mol. Biol. 22:361–366 (1993). Exemplary inducible promoters include, but are not limited to, that from the ACEI system which responds to copper (Mett et al., PNAS 90:4567–4571 (1993)); In2 gene from maize which responds to benzenesulfonamide herbicide safeners (Hershey et al., Mol. Gen Genetics 227:229–237 (1991) and Gatz et al., Mol. Gen. Genetics 243:32–38 (1994)) or Tet repressor from Tn10 (Gatz et al., Mol. Gen. Genetics 227:229–237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone (Schena et al., Proc. Natl. Acad. Sci. U.S.A. 88:0421 (1991)).

Constitutive Promoters

A constitutive promoter is operably linked to a gene for expression in cotton or the constitutive promoter is operably linked to a nucleotide sequence encoding a signal sequence which is operably linked to a gene for expression in cotton.

Many different constitutive promoters can be utilized in the instant invention. Exemplary constitutive promoters include, but are not limited to, the promoters from plant viruses such as the 35S promoter from CaMV (Odell et al., Nature 313:810–812 (1985)), the promoters from such genes as rice actin (McElroy et al., Plant Cell 2:163–171 (1990)); ubiquitin (Christensen et al., Plant Mol. Biol. 12:619–632 (1989) and Christensen et al., Plant Mol. Biol. 18:675–689 (1992)); pEMU (Last et al., Theor. Appl. Genet. 81:581–588 (1991)); MAS (Velten et al., EMBO J. 3:2723–2730 (1984)), maize H3 histone (Lepetit et al., Mol. Gen. Genetics 231: 276–285 (1992) and Atanassova et al., Plant Journal 2 (3): 291–300 (1992)), and the small subunit of the cotton ribulose biphosphate carboxlyase promoter (U.S. Pat. No. 6,040, 504, issued to Rice et al. on Mar. 21, 2000). Jhu et al. in U.S. Pat. No. 6,610,907, issued Aug. 26, 2003, discloses a cotton leaf curl virus bi-directional promoter and method of expressing a heterologous gene in various plant tissues at a high level using the promoter and AC2 protein factor from the CLCuV genome to include the expression level.

The ALS promoter, Xba1/Ncol fragment 5' to the *Brassica napus* ALS3 structural gene (or a nucleotide sequence similar to said Xba1/Ncol fragment), represents a particularly useful constitutive promoter. See PCT Application WO96/30530. The AHAS promoter is another useful promoter as described in Grula, J. W., Hudspeth, R. L., Hobbs, S. L., and Anderson, D. M., Plant Mol. Biol. 28:837–846 (1995).

Tissue-Specific or Tissue-Preferred Promoters

A tissue-specific promoter is operably linked to a gene for expression in cotton. Optionally, the tissue-specific promoter is operably linked to a nucleotide sequence encoding a signal sequence which is operably linked to a gene for expression in cotton. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention.

Exemplary tissue-specific or tissue-preferred promoters include, but are not limited to, a root-preferred promoter, such as that from the phaseolin gene (Murai et al., Science 23:476–482 (1983) and Sengupta-Gopalan et al., Proc. Natl. Acad. Sci. U.S.A. 82:3320–3324 (1985)); a leaf-specific and light-induced promoter such as that from cab or rubisco (Simpson et al., EMBO J. 4(11):2723–2729 (1985) and Timko et al., Nature 318:579–582 (1985)); an anther-specific promoter such as that from LAT52 (Twell et al., Mol. Gen. Genetics 217:240–245 (1989)); a pollen-specific promoter such as that from Zm13 (Guerrero et al., Mol. Gen. Genetics 244:161–168 (1993)), a microspore-preferred promoter such as that from apg (Twell et al., Sex. Plant Reprod. 6:217–224 (1993)), a heterologous genetic construct comprising a fiber-specific promoter and a coding sequence encoding a plant peroxidase (U.S. Pat. No. 5,608,148 to John on Mar. 4, 1997; U.S. Pat. No. 5,521,078 to John on May 28, 1996) or an 1144 bp 5' regulatory region comprising an 1108 bp promoter sequence and a 36 bp 5' transcribed, untranslated sequence from a cotton alpha-globulin gene (U.S. Patent Application 2003/0154516 to Rathore et al. Aug. 14, 2003). U.S. Pat. No. 6,566,586, issued to Stalker et al. on May 20, 2003, discloses a cotton promoter region from an expansin gene expressed in developing fibers. U.S. Pat. No. 6,329,570, issued to Martineau on Dec. 11, 2001, discloses cotton modification using ovary-tissue transcriptional factors directing gene expression in ovary tissue, particularly in very early fruit development to express genes encoding isopentenyl transferase to permit modification of the characteristics of boll set and provide a mechanism for altering fiber quality characteristics including fiber dimension and strength.

Signal Sequences for Targeting Proteins to Subcellular Compartments

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., Plant Mol. Biol. 20:49 (1992); Close, P. S., Master's Thesis, Iowa State University (1993); Knox et al., Plant Mol. Biol. 9:3–17 (1987); Lerner et al., Plant Physiol. 91:124–129 (1989); Fontes et al., Plant Cell 3:483–496 (1991); Matsuoka et al., Proc. Natl. Acad. Sci. 88:834 (1991); Gould et al., J. Cell. Biol. 108:1657 (1989); Creissen et al., Plant J. 2:129 (1991); Kaideron, et al., Cell 39:499–509 (1984); Steifel, et al., Plant Cell 2:785–793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein can then be extracted from a tissue of interest or from total biomass. Protein extraction from plant biomass can be accomplished by known methods which are discussed, for example, by Heney and Orr, Anal. Biochem. 114:92–6 (1981).

According to an embodiment, the transgenic plant provided for commercial production of foreign protein is a cotton plant. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology, CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant.

Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

Genes that Confer Resistance to Pests or Diseases

Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones et al., Science 266:789 (1994) (cloning of the tomato Cf-9 gene for resistance to *Cladosporium fulvum*); Martin et al., Science 262:1432 (1993) (tomato Pto gene for resistance to *Pseudomonas syringae* pv. tomato encodes a protein kinase); Mindrinos et al., Cell 78:1089 (1994) (*Arabidopsis* RSP2 gene for resistance to *Pseudomonas syringae*).

A gene conferring resistance to a pest, such as nematodes. See, e.g., PCT Applications WO96/30517 and WO093/19181.

A *Bacillus thuringiensis* protein, a derivative thereof or a synthetic polypeptide modeled thereon. See, for example, Geiser et al., Gene 48:109 (1986), who disclose the cloning and nucleotide sequence of a Bt delta-endotoxin gene. U.S. Pat. No. 5,608,142 to Barton et al. and issued Mar. 4, 1997 discloses insecticidal cotton plants wherein a plant expression vector causing expression of a truncated amino-terminal portion of *Bacillus thuringiensis* delta-endotoxin gene in plant cells, thereby conferring resistance to Lepidopterans. U.S. Pat. No. 5,885,963, issued to Stockhoff et al. on Mar. 23, 1999, discloses the use of B.t. isolate PS 123D1 and delta-endotoxins to control hemipterans. Moreover, DNA molecules encoding delta-endotoxin genes can be purchased from American Type Culture Collection, Manassas, Va., for example, under ATCC Accession Nos. 40098, 67136, 31995 and 31998.

U.S. Pat. No. 6,200,561, issued to Bilimoria on Mar. 13, 2001, discloses using viral protein extracts from *Chilo* iridescent virus to control insects such as the cotton boll weevil and cotton aphid.

A lectin. See, for example, the disclosure by Van Damme et al., Plant Molec. Biol. 24:25 (1994), who disclose the nucleotide sequences of several *Clivia miniata* mannose-binding lectin genes. U.S. Patent Application 2004/0016019 to Yenofski et al. Jan. 22, 2004 discloses chimeric genes encoding lectins (barley, havein, nettle) exhibiting pesticidal activity (e.g., insecticidal and/or fungicidal) and used to transform cotton.

A cotton event, PV-GHBK04 (757), when operably transformed into a cotton plant confers resistance to Lepidopterans. U.S. Patent Application 2003/0024005 to Hillyard et al. Jan. 30, 2003. Cotton cells transformed with a chimeric gene expressing a polypeptide with substantially the same insect toxicity properties of *Bacillus thuringiensis* were disclosed as toxic to Lepidopterans in U.S. Patent Application 2001/0026939 to Rice et al. Oct. 4, 2001. U.S. Patent Application 2004/0045054 to Beazlet et al. Mar. 4, 2004 discloses a 531 cotton event nucleic acid sequences conferring lepidopteran resistance.

A vitamin-binding protein such as avidin. See PCT application U.S. 93/06487. The application teaches the use of avidin and avidin homologues as larvicides against insect pests. An enzyme inhibitor, for example, a protease or proteinase inhibitor or an amylase inhibitor. See, for example, Abe et al., J. Biol. Chem. 262:16793 (1987) (nucleotide sequence of rice cysteine proteinase inhibitor), Huub et al., Plant Molec. Biol. 21:985 (1993) (nucleotide sequence of cDNA encoding tobacco proteinase inhibitor I), Sumitani et al., Biosci. Biotech. Biochem. 57:1243 (1993) (nucleotide sequence of *Streptomyces nitrosporeus* Alpha-amylase inhibitor) and U.S. Pat. No. 5,494,813 (Hepher and Atkinson, issued Feb. 27, 1996).

An insect-specific hormone or pheromone such as an ecdysteroid or juvenile hormone, a variant thereof, a mimetic based thereon, or an antagonist or agonist thereof. See, for example, the disclosure by Hammock et al., Nature 344:458 (1990), of baculovirus expression of cloned juvenile hormone esterase, an inactivator of juvenile hormone.

An insect-specific peptide or neuropeptide which, upon expression, disrupts the physiology of the affected pest. For example, see the disclosures of Regan, J. Biol. Chem. 269:9 (1994) (expression cloning yields DNA coding for insect diuretic hormone receptor), and Pratt et al., Biochem. Biophys. Res. Comm. 163:1243 (1989) (an allostatin is identified in *Diploptera puntata*). See also U.S. Pat. No. 5,266,317 to Tomalski et al., who disclose genes encoding insect-specific, paralytic neurotoxins.

An insect-specific venom produced by a snake, a wasp, etc. For example, see Pang et al., Gene 116:165 (1992), for disclosure of heterologous expression in plants of a gene coding for a scorpion insectotoxic peptide.

An enzyme responsible for hyper-accumulation of a monoterpene, a sesquiterpene, a steroid, a hydroxamic acid, a phenylpropanoid derivative or another non-protein molecule with insecticidal activity.

An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT Application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., Insect Biochem. Molec. Biol. 23:691 (1993), who teach the nucleotide sequence of a cDNA encoding tobacco hornworm chitinase, and Kawalleck et al., Plant Molec. Biol. 21:673 (1993), who provide the nucleotide sequence of the parsley ubi4-2 polyubiquitin gene.

A molecule that stimulates signal transduction. For example, see the disclosure by Botella et al., Plant Molec. Biol. 24:757 (1994), of nucleotide sequences for mung bean calmodulin cDNA clones, and Griess et al., Plant Physiol. 104:1467 (1994), who provide the nucleotide sequence of a maize calmodulin cDNA clone.

A hydrophobic moment peptide. See PCT Application WO95/16776 (disclosure of peptide derivatives of Tachyplesin which inhibit fungal plant pathogens) and PCT application WO95/18855 (teaches synthetic antimicrobial peptides that confer disease resistance).

A membrane permease, a channel former or a channel blocker. For example, see the disclosure of Jaynes et al., Plant Sci. 89:43 (1993), of heterologous expression of a cecropin-beta, lytic peptide analog to render transgenic tobacco plants resistant to *Pseudomonas solanacearum*.

A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., Ann. Rev. Phytopathol. 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

An insect-specific antibody or an immunotoxin derived therefrom. Thus, an antibody targeted to a critical metabolic function in the insect gut would inactivate an affected enzyme killing the insect. Cf. Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

A virus-specific antibody. See, for example, Tavladoraki et al., Nature 366:469 (1993), who show that transgenic plants expressing recombinant antibody genes are protected from virus attack.

A developmental-arrestive protein produced in nature by a pathogen or a parasite. Thus, fungal endo-α-1,4-D-polygalacturonases facilitate fungal colonization and plant nutrient release by solubilizing plant cell wall homo-alpha-1,4-D-galacturonase. See Lamb et al., Bio/Technology 10:1436 (1992). The cloning and characterization of a gene which encodes a bean endopolygalacturonase-inhibiting protein is described by Toubart et al., Plant J. 2:367 (1992).

A developmental-arrestive protein produced in nature by a plant. For example, Logemann et al., Bio/Technology 10:305 (1992), have shown that transgenic plants expressing the barley ribosome-inactivating gene have an increased resistance to fungal disease.

Genes that Confer Resistance to an Herbicide

An herbicide that inhibits the growing point or meristem, such as an imidazolinone or a sulfonylurea. Exemplary genes in this category code for mutant ALS and AHAS enzyme as described, for example, by Lee et al., EMBO J. 7:1241 (1988), and Miki et al., Theor. Appl. Genet. 80:449 (1990), respectively.

Glyphosate (resistance conferred by mutant 5-enolpyruvyl-shikimate-3-phosphate synthase (EPSP) and aroA genes, respectively) and other phosphono compounds such as glufosinate (phosphinothricin acetyl transferase (PAT) and *Streptomyces hygroscopicus* PAT, bar, genes), and pyridinoxy or phenoxy proprionic acids and cyclohexones (AC-Case inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai.

European Patent Application 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a PAT gene is provided in European Patent Application 0 242 246 to Leemans et al. DeGreef et al., Bio/Technology 7:61 (1989), describe the production of transgenic plants that express chimeric bar genes coding for PAT activity. Exemplary of genes conferring resistance to phenoxy proprionic acids and cyclohexones, such as sethoxydim and haloxyfop are the Acc1-S1, Acc1-S2 and Acc1-S3 genes described by Marshall et al., Theor. Appl. Genet. 83:435 (1992). See also U.S. Pat. Nos. 5,646,024 and 5,561,236, U.S. Patent Application 2003/0097687 to Trolinder et al. May 22, 2003. and Thompson et al., 1987, EMBO J. 6:2519–2523, Beglock et al., 1987, EMBO J. 6: 2513–2518.

An herbicide that inhibits photosynthesis, such as a triazine (psbA and gs+ genes) or a benzonitrile (nitrilase gene). Przibila et al., Plant Cell 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., Biochem. J. 285:173 (1992).

Genes that Confer or Contribute to a Value-Added Trait

Modified fatty acid metabolism, for example, by transforming a plant with an antisense gene of stearyl-ACP desaturase to increase stearic acid content of the plant. See Knultzon et al., Proc. Natl. Acad. Sci. U.S.A. 89:2624 (1992).

Enhanced fiber characteristics have been effected by transforming cotton cells with endoxyloglucan transferase, catalase and peroxidase, U.S. Patent Application 2003/0074697 to Allen et al., Apr. 17, 2003. DNA constructs to provide for modification of transcription of a DNA sequence in cotton fibers, particularly in very early fiber development are disclosed in U.S. Patent Application 2003/0106089 to McBride et al. Jun. 5, 2003. U.S. Patent Application 2003/0221218 to Wilkins Nov. 27, 2003 discloses plant fiber expansion (FE) genes encoding FI polypeptides, such as phosphoenol pyruvate carboxylase, expansin, endoglucanase, xyloglucan, endoglycosyltransferase, and pectin methyl esterase and fiber-specific promoters. U.S. Pat. No. 5,932,713 to Kasukabe et al. and issued Aug. 3, 1999 and U.S. Pat. No. 6,259,003, issued to Fujisawa et al. on Jul. 10, 2001, disclose cotton fiber tissue-specific genes specifically expressed in cotton fiber tissue at the stage of elongation, one of the genes derived from the genus *Gossypium* and found to change the degree of expression by treatment with a brassinosteroid. U.S. Pat. No. 6,168,174, issued to Hasegawa et al. on Jan. 2, 2001, discloses nucleotide sequences controlling fiber formation in cotton. U.S. Pat. No. 6,472,588, issued to Haigler et al. on Oct. 29, 2002, discloses transgenic cotton plants with altered fiber characteristics transformed with a sucrose phosphate synthase nucleic acid, wherein enhanced fiber strength, fiber length, fiber fineness, fiber maturity ratio, immature fiber content, fiber uniformity, and micronaire are enabled.

Modified carbohydrate composition effected, for example, by transforming plants with a gene coding for an enzyme that alters the branching pattern of starch. See Shiroza et al., J. Bacteriol. 170:810 (1988) (nucleotide sequence of *Streptococcus* mutants fructosyltransferase gene), Steinmetz et al., Mol. Gen. Genet 20:220 (1985) (nucleotide sequence of *Bacillus subtilis* levansucrase gene), Pen et al., Bio/Technology 10:292 (1992) (production of transgenic plants that express *Bacillus licheniformis* α-amylase), Elliot et al., Plant Molec. Biol. 21:515 (1993) (nucleotide sequences of tomato invertase genes), Søgaard et al., J. Biol. Chem. 268:22480 (1993) (site-directed mutagenesis of barley Alpha-amylase gene), Fisher et al., Plant Physiol. 102:1045 (1993) (maize endosperm starch branching enzyme II), and Haigler et al., Proc. Beltwide Cotton Prod. Res. Conf. p. 483 (2000) (transgenic cotton with improved fiber micronaire, strength and length and increased fiber weight).

Suppression of gossypol synthesis effected by a gene derived from cotton plants and encoding (+)-gamma-cadinene-8-hydroxylase. U.S. Patent Application 2002/0187538 to Essenberg et al. Dec. 12, 2002.

Methods for Cotton Transformation

Numerous methods for plant transformation have been developed, including biological and physical, plant transformation protocols. See, for example, Miki et al., "Procedures for Introducing Foreign DNA into Plants" in Methods in Plant Molecular Biology and Biotechnology, Glick B. R. and Thompson, J. E. Eds. (CRC Press, Inc., Boca Raton, 1993) pages 67–88. In addition, expression vectors and in vitro culture methods for plant cell or tissue transformation and regeneration of plants are available. See, for example, Gruber et al., "Vectors for Plant Transformation" in Methods in Plant Molecular Biology and Biotechnology, Glick B. R. and Thompson, J. E. Eds. (CRC Press, Inc., Boca Raton, 1993) pages 89–119; U.S. Pat. No. 5,986,181 to Trolinder et al. and issued Nov. 16, 1999 (in vitro regeneration of fertile *Gossypium* plants in which cells from the transition region tissue of seedlings is excised, cultured, then transformed (e.g., *Agrobacterium*) cells are regenerated into homogeneously by means of somatic embryogenesis in a hormone-free medium).

*Agrobacterium*-Mediated Transformation

One method for introducing an expression vector into plants is based on the natural transformation system of *Agrobacterium*. See, for example, Horsch et al., Science 227:1229 (1985). *A. tumefaciens* and *A. rhizogenes* are plant pathogenic soil bacteria which genetically transform plant cells. The Ti and R1 plasmids of *A. tumefaciens* and *A. rhizogenes*, respectively, carry genes responsible for genetic transformation of the plant. See, for example, Kado, C. I., Crit. Rev. Plant Sci. 10:1 (1991). Descriptions of *Agrobacterium* vector systems and methods for *Agrobacterium*-mediated gene transfer are provided by Gruber et al., supra, Miki et al., supra, U.S. Pat. No. 6,660,914, issued to Rangan et al. on Dec. 9, 2003, and Moloney et al., Plant Cell Reports 8:238 (1989). See also, U.S. Pat. No. 5,563,055 (Townsend and Thomas), issued Oct. 8, 1996. Transformation of cotton cells is disclosed in U.S. Patent Application 2003/0074697 to Allen et al. and published 17 Apr. 2003 and in U.S. Pat. No. 6,573,437, issued to Anderson et al. on Jun. 3, 2003.

Direct Gene Transfer

Several methods of plant transformation collectively referred to as direct gene transfer have been developed as an alternative to *Agrobacterium*-mediated transformation. A generally applicable method of plant transformation is microprojectile-mediated transformation wherein DNA is carried on the surface of microprojectiles measuring 1 to 4 micrometers. The expression vector is introduced into plant tissues with a biolistic device that accelerates the microprojectiles to speeds of 300 to 600 m/s which is sufficient to penetrate plant cell walls and membranes. Sanford et al., Part. Sci. Technol. 5:27 (1987), Sanford, J. C., Trends Biotech. 6:299 (1988), Klein et al., Bio/Technology 6:559–563 (1988), Sanford, J. C., Physiol. Plant 7:206 (1990), Klein et al., Biotechnology 10:268 (1992). See also U.S. Pat. No. 5,015,580 (Christou, et al.), issued May 14, 1991; U.S. Pat. No. 5,322,783 (Tomes, et al.), issued Jun. 21, 1994.

Another method for physical delivery of DNA to plants is sonication of target cells. Zhang et al., Bio/Technology 9:996 (1991). Alternatively, liposome and spheroplast fusion have been used to introduce expression vectors into plants. Deshayes et al., EMBO J., 4:2731 (1985), Christou et al., Proc. Natl. Acad. Sci. U.S.A. 84:3962 (1987). Direct uptake of DNA into protoplasts using $CaCl_2$ precipitation, polyvinyl alcohol or poly-L-ornithine have also been reported. Hain et al., Mol. Gen. Genet. 199:161 (1985) and Draper et al., Plant Cell Physiol. 23:451 (1982). Electroporation of protoplasts and whole cells and tissues have also been described. Donn et al., In Abstracts of Fifth International Congress on Plant Cell and Tissue Culture IAPTC, A2–38, p 53 (1990); D'Halluin et al., Plant Cell 4:1495–1505 (1992) and Spencer et al., Plant Mol. Biol. 24:51–61 (1994).

Yet another method is whisker-mediated transformation of embryogenic cotton suspension cultures, wherein agitation of the suspension culture in the presence of needle-like structures termed "whiskers" results in DNA uptake and integration by the culture cells. U.S. Patent Application 2002/0066121 to Kosege et al. May 30, 2002; U.S. Pat. No. 6,730,824, issued to Petolino et al. on May 4, 2004.

Following transformation of cotton target tissues, expression of the above-described selectable marker genes allows for preferential selection of transformed cells, tissues and/or plants, using regeneration and selection methods now well known in the art.

The foregoing methods for transformation would typically be used for producing a transgenic variety. The transgenic variety could then be crossed with another (non-transformed or transformed) variety in order to produce a new transgenic variety. Alternatively, a genetic trait which has been engineered into a particular cotton line using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties which do not contain that gene. As used herein, "crossing" can refer to a simple or single, or the process of backcrossing, depending on the context.

Single Gene Conversion

When the term cotton plant is used in the context of the present invention, this also includes any single gene conversions of that variety. The term single gene converted plant as used herein refers to those cotton plants which are developed by a plant breeding technique called backcrossing wherein essentially all of the desired morphological and physiological characteristics of a variety are recovered in addition to the single or relatively small number of desirable genes transferred into the variety via the backcrossing technique. Backcrossing methods can be used with the present invention to improve or introduce a characteristic into the variety. The term backcrossing as used herein refers to the repeated crossing of a hybrid progeny back to the recurrent parent, i.e., backcrossing 2, 3, 4, 5, 6, 7 or more times to the recurrent parent. The parental cotton plant which contributes the gene for the desired characteristic is termed the nonrecurrent or donor parent. This terminology refers to the fact that the nonrecurrent parent is used one time in the backcross protocol and therefore does not recur. The parental cotton plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a cotton plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol typically is to alter or substitute a single trait or characteristic in the original variety although more complex transfers are often designed and carried out. To accomplish this, a single gene of the recurrent variety is modified or substituted with the desired gene from the nonrecurrent parent, while retaining essentially all of the rest of the desired genetic, and therefore the desired physiological and morphological, constitution of the original variety. The choice of the particular nonrecurrent parent will depend on the purpose of the backcross; one of the major purposes is to add some commercially desirable and/or agronomically important trait to the plant. The exact backcrossing protocol will depend on the characteristic or trait being altered to determine an appropriate testing protocol.

Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new variety but that can be improved by backcrossing techniques. Single gene traits may or may not be transgenic, examples of these traits include, but are not limited to, male sterility, herbicide resistance, resistance for bacterial, fungal, or viral disease, insect resistance, male fertility, enhanced nutritional quality, industrial usage, yield stability and yield enhancement. These genes are generally inherited through the nucleus. Several of these single gene traits are described in U.S. Pat. Nos. 5,959,185; 5,973,234 and 5,977,445.

Tissue Culture

Further reproduction of the variety can occur by tissue culture and regeneration. Tissue culture of various tissues of cottons and regeneration of plants therefrom is well known and widely published as described in U.S. Pat. No. 6,242,257, issued to Tuli et al. on Jun. 5, 2001, U.S. Patent Application 2003/0143744, U.S. Pat. Nos. 5,244,802; 5,583,036; 5,834,292; 5,859,321; 5,874,662; 6,040,504; 6,573,437; 6,620,990; 6,624,344 and 6,660,914. For example, reference may be had to Komatsuda, T. et al., "Genotype X Sucrose Interactions for Somatic Embryogenesis in Soybean," Crop Sci. 31:333–337 (1991); Stephens, P. A., et al., "Agronomic Evaluation of Tissue-Culture-Derived Soybean Plants," Theor. Appl. Genet. (1991) 82:633–635; Komatsuda, T. et al., "Maturation and Germination of Somatic Embryos as Affected by Sucrose and Plant Growth Regulators in Soybeans *Glycine gracilis* Skvortz and *Glycine max* (L.) Merr." Plant Cell, Tissue and Organ Culture, 28:103–113 (1992); Dhir, S. et al., "Regeneration of Fertile Plants from Protoplasts of Soybean (*Glycine max* L. Merr.); Genotypic Differences in Culture Response," Plant Cell Reports (1992) 11:285–289; Pandey, P. et al., "Plant Regeneration from Leaf and Hypocotyl Explants of *Glycine-wightii* (W. and A.) VERDC. var. *longicauda*," Japan J. Breed. 42:1–5 (1992); and Shetty, K., et al., "Stimulation of In Vitro Shoot Organogenesis in *Glycine max* (Merrill.) by Allantoin and Amides," Plant Science 81:245–251 (1992); as well as U.S. Pat. No. 5,024,944 issued Jun. 18, 1991 to Collins et al., and U.S. Pat. No. 5,008,200 issued Apr. 16, 1991 to Ranch et al. A method of regeneration of cotton plants from somatic cells in suspension cultures is disclosed in U.S. Pat. No. 5,695,999 to Rangan et al. Dec. 9, 1997. U.S. Pat. No. 5,846,797, issued to Strickland on Dec. 8, 1998, discloses a method of regenerating transformed (e.g., *Agrobacterium*) cotton plants from explant tissue. Thus, another aspect of this invention is to provide cells which upon growth and differentiation produce cotton plants having the physiological and morphological characteristics of cotton variety HAMMER.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, pods, leaves, stems, roots, root tips, anthers, and the like. Means for preparing and maintaining plant tissue culture are well known in the art. By way of example, a tissue culture comprising organs has been used to produce regenerated plants. U.S. Pat. Nos. 5,959,185; 5,973,234 and 5,977,445, described certain techniques, the disclosures of which are incorporated herein by reference.

Methods of Production

This invention also is directed to methods for producing a cotton plant by crossing a first parent cotton plant with a second parent cotton plant wherein the first or second parent cotton plant is a cotton plant of the variety HAMMER. Further, both first and second parent cotton plants can come from the cotton variety HAMMER. Thus, any such methods using the cotton variety HAMMER are part of this invention: selfing, backcrosses, hybrid production, crosses to populations, and the like. All plants produced using cotton variety HAMMER as a parent are within the scope of this invention, including those developed from varieties derived from cotton variety HAMMER. Advantageously, the cotton variety could be used in crosses with other, different, cotton plants to produce first generation ($F_1$) cotton hybrid seeds and plants with superior characteristics. The variety of the invention can also be used for transformation where exogenous genes are introduced and expressed by the variety of the invention. Genetic variants created either through traditional breeding methods using variety HAMMER or through transformation of HAMMER by any of a number of protocols known to those of skill in the art are intended to be within the scope of this invention.

As used herein, the term plant includes plant cells, plant protoplasts, plant cell tissue cultures from which cotton plants can be regenerated, plant calli, plant clumps, and plant cells that are intact in plants or parts of plants, such as embryos, pollen, ovules, flowers, pods, leaves, roots, root tips, anthers, and the like.

Cotton Quality Definitions

Essentially all the physiological and morphological characteristics. A plant having "essentially all the physiological and morphological characteristics" means a plant having the physiological and morphological characteristics, except for the characteristics derived from the converted trait.

General

Cotton Seed (Seed): the seed of the cotton plant, found in the fruit of cotton plants (bolls), from the surface of which grow cotton fibers.

Cotton Fiber: A cotton fiber is produced from a single elongated plant cell found in the surface of the seedcoat on a cotton seed. The two basic types of cotton fibers found on a cotton seed seedcoat are called "lint" and "linters".

Cotton Lint (Lint): These are the longer fibers on the seed coat of a cotton seed that are typically removed from the seed by a cotton gin during the ginning process.

Cotton Linters (Linters): These are the short fibers, normally remaining on a cotton seed after the cotton ginning process, that the gin is unable to remove.

Seedcotton (Seed Cotton): refers to the harvested portion of the cotton crop containing the seed and fiber, and various field contaminants (trash), before being separated into the seed, lint and trash fractions during the ginning process of a cotton gin.

Cotton Gin (Gin): a mechanical device that separates the seedcotton harvested from a cotton crop into the lint and seed fractions.

Gin Turnout: is an expression of yield from a Cotton Gin, i.e., the amount of lint produced from a quantity of seedcotton. "Gin turnout" is defined as a fraction of lint in a machine harvested sample of seed cotton (lint, seed, and trash) expressed as a percentage.

Tex: A measuring unit for linear density of fibers or yarns expressed as mass in milligrams of one meter of fiber or yarn.

HVI: High Volume Instrumentation, an instrument system for cotton fiber that measures length, length uniformity, strength, elongation, micronaire and color.

AFIS: Advanced Fiber Information System, an instrument system for cotton fiber that measures length and length distribution, including % short fiber; fineness, maturity and foreign matter.

Individual Instruments: A collection of cotton fiber testing instruments generally including the following—Fibrograph measures length and length uniformity; Stelometer measures strength and elongation; Fibronaire measures micronaire; Arealometer measures fineness and maturity; Shirley analyzer measures trash or non-lint content.

Lint Percent: the proportion of the mass of lint to the mass of a clean seedcotton sample, expressed as a percentage.

Lint Percent is the lint (fiber) fraction of seed cotton (lint and seed).

Lint Yield: is the quantity of fiber produced on a given unit of land (usually expressed as pounds of lint per acre or kilograms of lint per hectare).

Seedcotton Yield (also Seed Cotton Yield): is the quantity of seedcotton produced on a given unit of land area (usually expressed as pounds of lint per acre or kilograms of lint per hectare).

Crop Maturity Rating (Crop Maturity): is defined as a visual rating near harvest on the amount of opened bolls on the plants of a variety.

Yarn Count (also known as Ne or denier)—A measure of the fineness of a yarn; the higher the count the finer the yarn. The relation between Tex and yarn is represented by the formula: Tex=592/count. For example a 22's count is equivalent to 27 Tex (or 592/22).

Fiber Length

Span Length: the distance spanned by a specific percentage of the fibers in the test specimen when the initial starting point of spanning is considered to be 100%

2.5% Span Length: Length in inches by 2.5% of the fibers scanned from the initial starting point. This measurement approximates the Classer's Staple Length.

50% Span Length: Length in inches by 50% of the fibers scanned from the initial starting point.

Mean Length: Mean length of fibers in the test specimen.

UHM: Upper Half Mean—this is the average length of the longest one-half of the fiber is the sample specimen. This is the HVI length measurement used in the USDA classing offices, and approximates also Classer's Staple Length.

HVI Fiber Length: UHM from the HVI system.

UQL: Upper Quartile Length of a fiber distribution as measured on the AFIS instrument system.

Length Uniformity

Uniformity Ratio: Ratio of 50% Span Length to 2.5% Span Length expressed as a percentage. The Fibrograph instrument is used in measuring this trait and values typically fall between 45 and 50%.

Uniformity Index: Ratio of Mean Length to UHM expressed as a percentage, and is provide from the HVI system. Values typically range in the low 80's.

HVI Uniformity: Uniformity Index from the HVI system.

Short Fiber Content: Percentage of fibers in a sample less than ½ inch long.

Fiber Strength

Strength, T1—Tensile strength of a fiber bundle measured on a stelometer with the jaws separated by ⅛ inch and expressed as centiNewtons, or cN, per tex (approximates grams per Tex). When calibrated to the International Standard, Acala values are typically in the low to mid-twenties.

HVI Strength—Expressed as grams per tex, usually calibrated to the USDA-AMS standard. These values are similar to the Stelometer instrument, but may be a third higher than the Stelometer T1 values defined above.

Elongation, E1—A measure of elasticity measured on the Stelometer or the HVI. Specifically the percentage elongation at break with the jaws holding the fiber bundle separated by ⅛ inch. The fiber sample usually stretches before it is broken during the strength measurement process, and elongation is a value reflecting the tendency to stretch.

Fiber Fineness

Arealometer—Perimeter of a fiber, in microns.

AFIS Fineness—Weight fineness, or linear density of a fiber defined as mass per unit length; expressed in millitex units.

AFIS Standard Fineness—Fineness in millitex adjusted for fiber maturity. Derived from the formula: Std Fineness=Fineness/Maturity ratio.

Fiber Perimeter: is a measure of the average circumference of the fibers in a lint sample expressed in microns.

Micronaire—Fineness and maturity of a sample expressed in standard micronaire units.

Fiber Maturity

Arealometer—Relative maturity of fibers in a sample, expressed as a percentage.

AFIS Maturity Ratio—Relative maturity of fibers in a sample, expressed as a ratio.

Micronaire—Fineness and maturity of a sample expressed in standard micronaire units.

Micronaire

Micronaire (Mic)—Fineness and maturity of a sample expressed in standard micronaire units. Micronaire values are provided by both the HVI system and the Fibronaire instrument, and the fiber characteristics of fineness and maturity are confounded in either of these test instrumentation.

HVI Micronaire (Mic) is a measure of the fineness and shape of the fiber and is determined by measuring the amount of constant pressure forced through a 50 gram sample of lint, the lint sample enclosed in a chamber of fixed volume. Within a cotton cultivar, micronaire is also a measure of maturity. Micronaire differences are governed by changes in perimeter, in cell wall thickness, or by changes in both. Within a variety, cotton perimeter is fairly constant and maturity will cause a change in micronaire. Consequently, micronaire has a high correlation with maturity within a variety of cotton. Maturity is the degree of development of cell wall thickness. Micronaire may not have a good correlation with maturity between varieties of cotton having different fiber perimeter. Micronaire values range from about 2.0 to 6.0:
- 1–2.9. Very fine. Possible small perimeter but mature (good fiber), or large perimeter but immature (bad fiber).
- 2.9–3.7. Fine. Various degrees of maturity and/or perimeter.
- 3.8–4.6. Average. Average degree of maturity and/or perimeter.
- 4.7–5.5. Coarse. Usually fully developed (mature), but larger perimeter.
- >5.5. Very coarse. Fully developed, large-perimeter fiber.

Color & Trash

Color Grade Index—Cotton classers color grade expressed as a color grade index where GM(11)=105; SM(21)=104; M(31)=100; SLM(41)=94; LM(51)=85. This conversion permits averaging.

Rd—An instrument measure of percentage reflectance; the higher the value the brighter the cotton.

B+—Hunters value—An instrument measure of increasing yellowness. The combination of Rd and +B values defines the color grade as measured by instrument.

Leaf grade—Classers estimate of leaf trash. No's 1 through 7 indicate increasing amounts of trash.

Non-lint %—Percent trash or foreign matter measured on the Shirley Analyzer.

SCF—seed coat fragments.

Yarn Strength

Yarn Tenacity (Yten)—skein strength of 22's count yarns spun from a miniature 50 gram sample, adjusted to standard skein basis and measured in milliNewtons per tex (mN/Tex).

CSP (count strength product)—Product of strength (in pounds) of a standard skein multiplied by the yarn count. Also known as Break Factor.

Break Factor—same as CSP.

Spin Potential (SPY)—The finest yarn count into which a fiber sample can be spun without excessive breakage, or Ends Down.

Single Yarn Elongation—Percentage elongation of yarn at break, similar to fiber elongation.

Manufacturing Waste

Picker and Card Waste—Percentage waste extracted from cotton lint by picking and carding, composed primarily of foreign matter.

Comber Waste—Percentage waste extracted from combers, composed primarily of short fibers.

Picker Card and Comber Waste—Total manufacturing waste.

Yarn Appearance & Imperfections

Neps—Number of neps per 1000 yards of yarn.

Thick Places—Number of thick places (other than neps) per 1000 yards of yarn.

Thin Places—Number of thin places per 1000 yards of yarn.

CV % (Coefficient of Variability for Yarns)—A statistical measure of yarn uniformity based on the above imperfections. The lower the CV % values the more even the yarn. (This is different from the CV values at the end of all the data tables, which describe the random or unaccounted for variability between samples).

Appearance Index (AI)—Visual estimate of yarn evenness. Higher numbers indicate smoother yarn.

Hammer

Hammer was compared to Acala Maxxa (the SJVCB Standard) and Phytogen 72 in 36 test locations over six years (Tables 1–8). Hammer is most similar to Acala Maxxa.

However, Hammer is distinctly different from both Maxxa and Phytogen 72 in having higher lint yield, gin turn-out, lint percent. Moreover, Hammer has lower fiber length and yarn strength than either variety.

In summary, Hammer is a novel cotton variety because of its significantly higher lint yield, gin turn-out, lint percent, and lower fiber length and yarn strength when compared to Acala Maxxa.

TABLE 1

2001–2003 CPCSD Advanced Strain Test

| Variety | Lint Yield Average (lbs/A) | Gin Turn Out (%) | Lint Percent (%) | 2.5% Length (in) | Yarn Str. (g/tex) |
|---|---|---|---|---|---|
| Maxxa | 1384 | 33.1 | 38.9 | 1.177 | 141.0 |
| Phy72 | 1580 | 31.9 | 37.4 | 1.210 | 139.8 |
| Hammer | 1754 | 38.5 | 44.9 | 1.104 | 133.2 |
| LSD.05 | 99 | 0.8 | 0.7 | 0.018 | 5.1 |
| CV % | 11.1 | 9.4 | 11.9 | 4.1 | 5.3 |

TABLE 2

2003 CPCSD Advanced Strain Test - Six Location Averages

| Variety | Lint Yield Average (lbs/A) | Seed Cotton Yield (lbs/A) | Gin Turn Out (%) | Fiber Traits | | | | | Yarn Str. (g/tex) |
|---|---|---|---|---|---|---|---|---|---|
| | | | | 2.5% length (in) | Unif. Ratio | T1 (g/tex) | E1 (%) | Mic | |
| Maxxa | 1296 | 4010 | 31.7 | 1.166 | 49.2 | 26.6 | 8.5 | 4.16 | 136.3 |
| Phy72 | 1561 | 5032 | 30.5 | 1.213 | 48.2 | 27.5 | 9.7 | 4.26 | 134.4 |
| Hammer | 1749 | 4611 | 37.6 | 1.093 | 50.0 | 25.7 | 8.7 | 4.50 | 126.3 |
| LSD.05 | 77 | 183 | 0.7 | 0.013 | 0.6 | 0.7 | 0.4 | 0.14 | 4.1 |
| CV % | 5 | 4 | 1.7 | 1.163 | 1.2 | 2.6 | 4.7 | 3.49 | 2.5 |

TABLE 3

2002 CPCSD Advanced Strain Test - Six Location Averages

| Variety | Lint Yield Average (lbs/A) | Seed Cotton Yield (lbs/A) | Gin Turn Out (%) | Fiber Traits | | | | | Yarn Str. (g/tex) |
|---|---|---|---|---|---|---|---|---|---|
| | | | | 2.5% length (in) | Unif. Ratio | T1 (g/tex) | E1 (%) | Mic | |
| Maxxa | 1491 | 4490 | 33.1 | 1.181 | 48.5 | 24.9 | 8.9 | 3.88 | 150.9 |
| Phy72 | 1637 | 5123 | 32.1 | 1.215 | 46.8 | 25.6 | 10.4 | 4.00 | 146.4 |
| Hammer | 1846 | 4863 | 37.9 | 1.106 | 48.5 | 24.5 | 9.1 | 4.12 | 140.8 |
| LSD.05 | 99 | 290 | 0.73 | 0.012 | 0.7 | 0.74 | 0.41 | 0.18 | 8.3 |
| CV % | 6.3 | 6.3 | 1.8 | 1.7 | 2.5 | 3.8 | 6.5 | 6.1 | 4.7 |

TABLE 4

2001 CPCSD Advanced Strain Test - Six Location Averages

| Variety | Lint Yield Average (lbs/A) | Seed Cotton Yield (lbs/A) | Gin Turn Out (%) | Fiber Traits | | | | | Yarn Str. (g/tex) |
|---|---|---|---|---|---|---|---|---|---|
| | | | | 2.5% length (in) | Unif. Ratio | T1 (g/tex) | E1 (%) | Mic | |
| Maxxa | 1364 | 3971 | 34.5 | 1.184 | 48.2 | 25.0 | 6.8 | 4.22 | 135.7 |
| Phy72 | 1543 | 4661 | 33.2 | 1.202 | 47.7 | 25.1 | 8.4 | 4.39 | 138.7 |
| Hammer | 1668 | 4184 | 40.0 | 1.110 | 48.4 | 24.2 | 7.3 | 4.38 | 132.4 |
| LSD.05 | 75 | 202 | 0.8 | 0.013 | 0.6 | 0.7 | 0.3 | 0.13 | 8.7 |
| CV % | 5.2 | 5.0 | 1.6 | 1.4 | 1.7 | 3.5 | 6.2 | 4.2 | 3.5 |

TABLE 5

2000 CPCSD Preliminary Strain Test - Four Location Averages

| Variety | Lint Yield Average (lbs/A) | Seed Cotton Yield (lbs/A) | Gin Turn Out (%) | Fiber Traits | | | | | Yarn Str. (g/tex) |
|---|---|---|---|---|---|---|---|---|---|
| | | | | 2.5% length (in) | Unif. Ratio | T1 (g/tex) | E1 (%) | Mic | |
| Maxxa | 1489 | 4175 | 35.6 | 1.17 | 55.8 | 22.9 | 5.75 | 4.30 | 145.1 |
| GTO Maxxa | 1547 | 4109 | 37.6 | 1.21 | 59.3 | 24.3 | 6.88 | 4.25 | 147.7 |
| Hammer | 1906 | 4621 | 41.3 | 1.11 | 54.3 | 23.8 | 6.50 | 4.60 | 127.3 |
| LSD.05 | 146.3 | 350.0 | 1.5 | 0.04 | 3.1 | 2.0 | 0.79 | 2.05 | 7.4 |
| CV % | 8.2 | 8.8 | 3.5 | 2.8 | 3.0 | 6.3 | 7.7 | 8.3 | 6.1 |

TABLE 6

1999 CPCSD Lines Test - Tulare Location

| Variety | Lint Yield Average (lbs/A) | Seed Cotton Yield (lbs/A) | Gin Turn Out (%) | Fiber Traits | | | | | Yarn Str. (g/tex) |
|---|---|---|---|---|---|---|---|---|---|
| | | | | 2.5% length (in) | Unif. Ratio | T1 (g/tex) | E1 (%) | Mic | |
| Maxxa | 1550 | 4453 | 34.8 | 1.21 | 47.9 | 22.3 | 8.0 | 4.20 | 129.7 |
| GTO Maxxa | 1540 | 4064 | 37.9 | 1.19 | 47.1 | 22.2 | 7.8 | 4.10 | 134.9 |
| Hammer | 2015 | 4854 | 41.5 | 1.13 | 49.6 | 22.8 | 7.3 | 4.40 | 121.7 |
| LSD.05 | 97 | 263 | 0.6 | 0.02 | 1.6 | 1.1 | 0.8 | 4.40 | 7.7 |
| CV % | 4.1 | 5.6 | 1.1 | 2.3 | 4.3 | 5.1 | 7.5 | 4.0 | 6.6 |

TABLE 7

2003 CPCSD Variety Test - Four Locations

Fiber Properties (across locations)

| Variety | Average (lbs/A) | (cv) | Gin Turn Out (%) | 2.5% length (in) | Unif. Ratio | T1 (g/tex) | E1 | Mic |
|---|---|---|---|---|---|---|---|---|
| Maxxa | 1291 | 5.0 | 30.3 | 1.175 | 49.4 | 26.4 | 8.0 | 4.05 |
| Phy 72 | 1501 | 12.7 | 29.7 | 1.215 | 48.8 | 27.4 | 9.4 | 4.42 |
| Summit | 1455 | 2.4 | 32.2 | 1.194 | 49.2 | 27.1 | 7.9 | 4.26 |
| Ultima | 1330 | 4.1 | 33.3 | 1.231 | 50.3 | 27.4 | 8.1 | 4.03 |
| Hammer | 1758 | 5.8 | 36.7 | 1.108 | 50.6 | 25.3 | 8.3 | 4.31 |
| LSD | 130 | | 1.7 | 0.022 | 1.0 | 1.0 | 0.5 | 0.32 |
| CV | 7.7 | | 7.3 | 1.5 | 1.7 | 3.1 | 4.8 | 6.6 |

TABLE 8

2002 CPCSD Variety Test - Four Locations

Fiber Properties (across locations)

| Variety | Average (lbs/A) | (cv) | Gin Turn Out (%) | 2.5% length (in) | Unif. index | T1 (g/tex) | E1 | Mic | Yarn Str. (g/tex) |
|---|---|---|---|---|---|---|---|---|---|
| Maxxa | 1583 | 12.4 | 31.8 | 1.18 | 0.51 | 26.3 | 8.1 | 4.2 | 150 |
| Phy72 | 1721 | 17.1 | 31.4 | 1.22 | 0.50 | 26.9 | 9.7 | 4.5 | 143 |
| GTO | 1666 | 10.7 | 35.1 | 1.21 | 0.51 | 26.5 | 8.4 | 4.2 | 156 |
| Summit | 1684 | 13.7 | 32.6 | 1.21 | 0.51 | 25.7 | 7.8 | 4.3 | 157 |
| Ultima | 1561 | 12.0 | 33.1 | 1.26 | 0.52 | 28.3 | 7.8 | 4.3 | 163 |
| B6736 | 1841 | 9.7 | 36.3 | 1.12 | 0.52 | 24.8 | 7.8 | 4.5 | 145 |
| LSD | 110 | | 1.4 | 0.02 | 0.01 | 0.8 | 0.4 | 0.3 | 7 |
| CV | 5.8 | | 2.4 | 2.5 | 2.5 | 3.3 | 5.0 | 4.8 | 2.6 |

Morphological Information.

Table 9 has the expressions of HAMMER, Phytogen 72, and Maxxa for enumerated morphological traits. As can be seen, HAMMER can be distinguished from the other varieties on the basis of its expressions of these traits.

TABLE 9

Morphological Descriptors.
Species: G. hirsutum
Area(s) of Adaptation: San Joaquin

| | HAMMER | Phytogen 72 | Maxxa |
|---|---|---|---|
| General | | | |
| Plant Habit[1] | I | I | I |
| Foliage[2] | I | I | I |
| Stem Lodging[3] | I | I | I |
| Fruiting Branch[4] | N | N | N |
| Growth[5] | Intermed | Intermed | Intermed |
| Leaf Color[6] | DG | LG | DG |
| Boll Shape[7] | More | More | More |
| Boll Breadth[8] | Middle | Middle | Middle |
| Days 50% Open Bolls | 144 | 147 | 150 |
| Cm to 1st Fruiting Branch[9] | 20.2 | 22.5 | 22.2 |
| No. Nodes to 1st Fruiting Branch[10] | 4.5 | 4.9 | 4.7 |
| Mature Plant Height[11] | 85.5 | 91.6 | 81.9 |
| Leaf Type[12] | N | N | N |
| Leaf Pubescence[13] | M | M | M |
| Leaf Nectaries[14] | P | P | P |
| Stem Pubescence[15] | I | G | I |
| Leaf Glands[16] | N | N | N |
| Stem Glands[17] | N | N | N |
| Caly % Lobe[18] | A | A | A |
| Petal Color[19] | C | C | C |
| Pollen Color[20] | C | C | C |
| Petal Spot[21] | A | A | A |
| Seed Index[22] | 11.8 | 11.4 | 11.4 |
| Lint Index[23] | 10.4 | 7.3 | 8.9 |
| Lint Percent[24] | 46.2 | 38.8 | 39.7 |
| Gin Turnout[25] | 39.9 | 32.5 | 34.0 |
| No. Seeds per Boll | 26.5 | 29.5 | 27.3 |
| Grams Seed per Boll | 5.3 | 5.6 | 5.7 |
| Locules per Boll | 4–5 | 4–5 | 4–5 |
| Boll Type[26] | Open | Open | Open |
| Fiber Properties[27] | | | |
| Fiber Length[28] | 1.12 | 1.22 | 1.175 |
| Fiber Uniformity[29] | 53.2 | 51.0 | 51.5 |
| Fiber Strength, T1[30] | 26.5 | 29.5 | 27.3 |
| Fiber Elongation, E1[31] | 8.2 | 9.7 | 8.8 |
| Micronaire | 3.91 | 4.3 | 4.16 |
| Yarn Strength[32] | 133 | 134 | 137 |

TABLE 9-continued

Morphological Descriptors.
Species: *G. hirsutum*
Area(s) of Adaptation: San Joaquin

|  | HAMMER | Phytogen 72 | Maxxa |
|---|---|---|---|
| Verticillium Wilt[33] | R | MR | R |
| Root-Knot Nematode[34] | MS | NT | S |

[1]S = Spreading, I = Intermediate, C = Compact;
[2]S = Sparse, I = Intermediate, D = Dense;
[3]L = Lodging, I = Intermediate, E = Erect;
[4]C = Clustered, S = Short, N = Normal;
[5]D = Determinate, Intermed = Intermediate, I = Indeterminate;
[6]GY = Greenish Yellow, LG = Light Green, MG = Medium Green, DG = Dark Green;
[7]LESS = Length Less Than Width, EQUAL = Length Equal to Width, MORE = Length More Than Width;
[8]BASE = Broadest At Base, Middle = Broadest At Middle;
[9]From Cotyledonary Node;
[10]Excluding Cotyledonary Node;
[11]From Cotyledonary Node;
[12]N = Normal Sub Okra, O = Okra, S = Super Okra;
[13]A = Absent, S = Sparse, M = Medium, D = Dense;
[14]P = Present, A = Absent;
[15]G = Glabrous, I = Intermediate, H = Hairy;
[16,17,18]A = Gossypol Absent, S = Gossypol Sparse, N = Gossypol Normal, M = Gossypol More Than Normal;
[19,20]C = Cream, Y = Yellow;
[21]P = Present, A = Absent;
[22]g/100 seed, fuzzy basis;
[23]g lint/100 seeds;
[24]Picked;
[25]Picked;
[26]S = Stormproof, Strom Resistant, Open;
[27]Individual Method;
[28]Inches, 2.5% SL;
[29]%;
[30]g/tex stelometer;
[31]%;
[32]lbs. 22's;
[33,34]S = Susceptible, MS = Moderately Susceptible, MR = Moderately Resistant, R = Resistant, NT = Not Tested.

Molecular Information

Materials and Methods

Plant Material and Primers

Silica gel dried leaf tissues were used for DNA extraction. DNA extractions were performed according to DNA Landmarks standard protocols; however persons of ordinary skill in the art will readily recognize that any of several extraction protocols can be followed to achieve satisfactory results. Purified DNA from 10 individual plants of the same line was then diluted to a concentration of 25 ng/μL and used directly for PCR amplification. Reverse primers were purchased from Invitrogen while forward primers were from Applied Biosystems. All forward primers were labeled with one of the 4 fluorescent dyes available for this technology (FAM, NED, VIC or PET). PCR reactions were amplified at an annealing temperature of 57° C.

Data Collection and Scoring

Detection of amplified fragments was performed on an ABI 3700 DNA sequencer (Applied Biosystems). Fragment sizes were generated by GeneScan software (Applied Biosystems) based on an internal size standard (GS-500) loaded with each sample. The relative size of each detected fragment was then binned into categories to associate an allele size to this specific fragment using Genotyper software (Applied Biosystems). Each bin was defined as being ±0.7 bp apart from any given allele size for a specific marker. Any data falling outside this range were reanalyzed and binned manually or declared "failed" by the scorer. All failed reactions were repeated at least once to retrieve a maximum of data points per marker.

Results

Table 10 contains the genotyping scores for all loci on all lines. Missing data are indicated by the digit "9." HAMMER can be distinguished from GTO and Maxxa on the basis of its expression of these SSR Marker alleles.

TABLE 10

Genotype Scores for SSR Marker Loci For HAMMER, GTO and Maxxa.

| marker | allele | GTO | Hammer | Maxxa |
|---|---|---|---|---|
| BNL0119 | 198 | 0 | 0 | 0 |
|  | 211 | 1 | 1 | 1 |
| BNL1053 | 175 | 0 | 0 | 0 |
|  | 177 | 1 | 1 | 1 |
|  | 192 | 1 | 1 | 1 |
| BNL1231 | 188 | 0 | 0 | 0 |
|  | 190 | 1 | 1 | 1 |
| BNL1317 | 174 | 0 | 0 | 0 |
|  | 209 | 0 | 0 | 0 |
|  | 190 | 0 | 0 | 0 |
|  | 182 | 1 | 1 | 1 |
|  | 201 | 1 | 1 | 1 |
|  | 192 | 0 | 0 | 0 |
| BNL2495 | 186 | 0 | 0 | 0 |
|  | 191 | 1 | 1 | 1 |
|  | 195 | 0 | 0 | 1 |
| BNL2646 | 96 | 1 | 1 | 1 |
|  | 112 | 0 | 0 | 0 |
|  | 143 | 1 | 1 | 1 |
|  | 120 | 0 | 0 | 0 |
| BNL3031 | 149 | 0 | 0 | 0 |
|  | 193 | 0 | 0 | 0 |
|  | 156 | 1 | 1 | 0 |
|  | 160 | 1 | 0 | 1 |
|  | 185 | 0 | 1 | 0 |
| BNL4030 | 112 | 0 | 0 | 0 |
|  | 116 | 0 | 0 | 0 |
|  | 114 | 1 | 1 | 1 |
|  | 110 | 0 | 0 | 0 |
| BNL4082 | 161 | 0 | 0 | 0 |
|  | 167 | 0 | 0 | 0 |
|  | 171 | 1 | 1 | 1 |
| BNL830 | 98 | 1 | 1 | 1 |
| C2135 | 181 | 0 | 0 | 0 |
|  | 188 | 0 | 0 | 0 |
|  | 159 | 1 | 1 | 1 |
|  | 179 | 1 | 1 | 1 |
|  | 209 | 1 | 1 | 1 |
|  | 168 | 0 | 0 | 0 |
|  | 204 | 0 | 0 | 0 |
|  | 220 | 0 | 0 | 0 |
| C29B | 168 | 0 | 0 | 0 |
|  | 171 | 0 | 0 | 0 |
|  | 156 | 1 | 1 | 1 |
| CIR030 | 268 | 0 | 0 | 0 |
|  | 273 | 1 | 1 | 1 |
|  | 270 | 0 | 0 | 0 |
| CIR062 | 189 | 0 | 0 | 0 |
|  | 195 | 0 | 0 | 0 |
|  | 179 | 1 | 1 | 1 |
|  | 193 | 1 | 1 | 1 |
| CIR081 | 225 | 0 | 0 | 0 |
|  | 221 | 1 | 1 | 1 |
|  | 223 | 0 | 0 | 0 |
| CIR099 | 85 | 1 | 1 | 1 |
|  | 87 | 0 | 0 | 0 |
|  | 83 | 0 | 0 | 0 |
| CIR148 | 136 | 0 | 0 | 0 |
|  | 147 | 1 | 1 | 1 |
|  | 157 | 0 | 0 | 0 |
|  | 144 | 0 | 0 | 0 |
| CIR170 | 157 | 1 | 1 | 1 |
|  | 161 | 0 | 0 | 0 |

TABLE 10-continued

Genotype Scores for SSR Marker Loci For HAMMER, GTO and Maxxa.

| marker | allele | GTO | Hammer | Maxxa |
|---|---|---|---|---|
| CIR196 | 185 | 0 | 0 | 0 |
|  | 191 | 1 | 1 | 1 |
|  | 187 | 1 | 1 | 1 |
| CIR209 | 134 | 0 | 0 | 0 |
|  | 154 | 0 | 1 | 1 |
|  | 157 | 1 | 0 | 1 |
| CIR228 | 191 | 0 | 0 | 0 |
|  | 215 | 0 | 0 | 0 |
|  | 219 | 1 | 1 | 1 |
|  | 223 | 0 | 0 | 0 |
|  | 220 | 0 | 0 | 1 |
|  | 197 | 0 | 0 | 0 |
| CIR234 | 262 | 1 | 1 | 1 |
|  | 276 | 0 | 0 | 0 |
|  | 279 | 1 | 1 | 1 |
|  | 285 | 0 | 0 | 0 |
|  | 291 | 1 | 1 | 1 |
| CIR246 | 149 | 0 | 0 | 0 |
|  | 153 | 0 | 0 | 0 |
|  | 157 | 1 | 1 | 1 |
|  | 167 | 0 | 0 | 0 |
| CIR261 | 276 | 0 | 0 | 0 |
|  | 278 | 1 | 1 | 1 |
| CIR286 | 119 | 0 | 0 | 0 |
|  | 125 | 1 | 1 | 1 |
|  | 131 | 1 | 1 | 1 |
|  | 137 | 0 | 0 | 0 |
| CIR293 | 314 | 0 | 0 | 0 |
|  | 304 | 1 | 1 | 1 |
|  | 302 | 0 | 0 | 0 |
| CIR307 | 170 | 1 | 1 | 1 |
|  | 180 | 0 | 0 | 0 |
| CIR329 | 261 | 1 | 1 | 1 |
|  | 267 | 0 | 0 | 0 |
|  | 275 | 0 | 1 | 1 |
|  | 281 | 1 | 0 | 1 |
|  | 253 | 0 | 0 | 0 |
|  | 249 | 0 | 0 | 1 |
| CIR338 | 157 | 1 | 1 | 1 |
| CIR369 | 198 | 0 | 0 | 0 |
|  | 200 | 1 | 1 | 1 |
| CIR381 | 237 | 0 | 0 | 0 |
|  | 264 | 0 | 0 | 0 |
|  | 262 | 0 | 0 | 0 |
|  | 246 | 1 | 1 | 1 |
|  | 266 | 1 | 1 | 1 |
|  | 274 | 0 | 0 | 0 |
| COTTON004 | 129 | 1 | 1 | 1 |
|  | 139 | 1 | 1 | 1 |
| COTTON019 | 130 | 0 | 0 | 0 |
|  | 128 | 1 | 1 | 1 |
| COTTON059 | 211 | 1 | 1 | 1 |
|  | 221 | 0 | 0 | 0 |
| COTTON079 | 117 | 0 | 0 | 0 |
|  | 139 | 1 | 1 | 1 |
|  | 140 | 0 | 0 | 0 |
| COTTON130 | 137 | 0 | 0 | 0 |
|  | 169 | 0 | 0 | 0 |
|  | 140 | 1 | 1 | 1 |
|  | 164 | 1 | 0 | 1 |
|  | 163 | 0 | 1 | 0 |
|  | 136 | 0 | 0 | 0 |
| DC20058 | 201 | 0 | 0 | 0 |
|  | 207 | 1 | 1 | 1 |
|  | 213 | 1 | 1 | 1 |
|  | 219 | 0 | 0 | 0 |
| DC20094 | 226 | 0 | 0 | 0 |
|  | 235 | 0 | 0 | 0 |
|  | 223 | 1 | 1 | 1 |
| DC30102 | 169 | 1 | 1 | 1 |
|  | 182 | 1 | 0 | 1 |
|  | 188 | 0 | 1 | 1 |
| DC40017 | 330 | 0 | 0 | 0 |
|  | 329 | 1 | 1 | 1 |
| DC40080 | 237 | 1 | 1 | 1 |
|  | 241 | 0 | 0 | 0 |
|  | 251 | 1 | 1 | 1 |
|  | 242 | 0 | 0 | 0 |
| DC40175 | 221 | 0 | 0 | 0 |
|  | 223 | 1 | 1 | 1 |
|  | 247 | 1 | 1 | 1 |
| DC40266 | 322 | 0 | 0 | 0 |
|  | 333 | 1 | 1 | 1 |
| DC40281 | 335 | 0 | 9 | 0 |
|  | 333 | 0 | 9 | 0 |
|  | 346 | 1 | 9 | 1 |
| DC40434 | 334 | 0 | 0 | 0 |
|  | 337 | 0 | 0 | 0 |
|  | 343 | 0 | 0 | 0 |
|  | 351 | 1 | 1 | 1 |
|  | 340 | 1 | 1 | 1 |
| DC40435 | 280 | 0 | 0 | 0 |
|  | 287 | 1 | 1 | 1 |
|  | 284 | 0 | 0 | 0 |
| JESPR204 | 163 | 0 | 0 | 0 |
|  | 171 | 1 | 1 | 1 |
|  | 193 | 0 | 0 | 0 |
|  | 187 | 1 | 1 | 1 |
|  | 190 | 0 | 0 | 0 |
| JESPR251 | 67 | 0 | 0 | 0 |
|  | 85 | 1 | 1 | 1 |

Deposit Information

A deposit of the California Planting Cotton Seed Distributors proprietary cotton cultivar HAMMER disclosed above and recited in the appended claims has been made with the American Type Culture Collection (ATCC), 10801 University Boulevard, Manassas, Va. 20110. The date of deposit was 21 Feb. 2007. The deposit of 2,500 seeds was taken from the same deposit maintained by California Planting Cotton Seed Distributors since prior to the filing date of this application. All restrictions upon the deposit have been removed, and the deposit is intended to meet all of the requirements of 37 C.F.R. § 1.801–1.809. The ATCC accession number is PTA-8217. The deposit will be maintained in the depository for a period of 30 years, or 5 years after the last request, or for the effective life of the patent, whichever is longer, and will be replaced as necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A seed of cotton cultivar designated HAMMER, representative seed of said cultivar having been deposited under ATCC Accession Number PTA-8217.

2. A cotton plant, or a regenerable part thereof, produced by growing the seed of claim 1.

3. A tissue culture of regenerable cells produced from the plant of claim 2.

4. A protoplast produced from the tissue culture of claim 3.

5. The tissue culture of claim 3, wherein cells of the tissue culture are from a plant part selected from the group consisting of leaf, pollen, embryo, root, root tip, anther, pistil, flower, seed, boll and stem.

6. A cotton plant regenerated from the tissue culture of claim 3, said plant having all the morphological and physiological characteristics of cotton cultivar HAMMER, representative seed of said cultivar having been deposited under ATCC Accession Number PTA-8217.

7. A method for producing a hybrid cotton seed wherein the method comprises crossing the plant of claim 2 with a different cotton plant and harvesting the resultant hybrid cotton seed.

8. A hybrid cotton seed produced by the method of claim 7.

9. A hybrid cotton plant, or a regenerable part thereof produced by growing said hybrid seed of claim 8.

10. A method of producing an herbicide resistant cotton plant wherein the method comprises transforming the cotton plant of claim 2 with a transgene that confers herbicide resistance.

11. An herbicide resistant cotton plant produced by the method of claim 10.

12. The cotton plant of claim 11, wherein the transgene confers resistance to an herbicide selected from the group consisting of imidazolinone, sulfonylurea., glyphosate, glufosinate, L-phosphinothricin, triazine and benzonitrile.

13. A method of producing an insect resistant cotton plant wherein the method comprises transforming the cotton plant of claim 2 with a transgene that confers insect resistance.

14. An insect resistant cotton plant produced by the method of claim 13.

15. The cotton plant of claim 14 wherein the transgene encodes a *Bacillus thuringiensis endotoxin*.

16. A method of producing a disease resistant cotton plant wherein the method comprises transforming the cotton plant of claim 2 with a transgene that confers disease resistance.

17. A disease resistant cotton plant produced by the method of claim 16.

18. A method of introducing a desired trait into cotton cultivar HAMMER wherein the method comprises:

crossing HAMMER plants grown from HAMMER seed, representative seed of which has been deposited under ATCC Accession Number PTA-8217, with plants of another cotton line that comprise a desired trait to produce progeny plants, wherein the desired trait is selected from the group consisting of male sterility, herbicide resistance, insect resistance and disease resistance;

selecting progeny plants that have the desired trait to produce selected progeny plants;

crossing the selected progeny plants with the HAMMER plants to produce backcross progeny plants;

selecting for backcross progeny plants that have the desired frail and physiological and morphological characteristics of cotton cultivar HAMMER to produce selected backcross progeny plants; and repeating said crossing and selecting for backcross progeny plants steps at least three times in succession, or, when using molecular markers, repeating said crossing and selecting at least once and selfing said backcross progeny plants at least once, to produce respective selected fourth or higher backcross progeny plants or second-selfed backcross progeny plants that comprise the desired trait and essentially all of the physiological and morphological characteristics of cotton cultivar HAMMER.

19. A plant produced by the method of claim 18, wherein the plant has the desired trait and essentially all of the physiological and morphological characteristics of cotton cultivar HAMMER as determined at the 5% significance level when grown in the same environmental conditions.

20. The plant of claim 19 wherein the desired trait is herbicide resistance and the resistance is conferred to an herbicide selected from the group consisting of imidazolinone, sulfonylurea, glyphosate, glufosinate, L-phosphinothricin, triazine and benzonitrile.

21. The plant of claim 19 wherein the desired trait is insect resistance and the insect resistance is conferred by a transgene encoding a *Bacillus thuringiensis* endotoxin.

22. A process of developing a cotton variety, comprising sequentially inbreeding segregating generations of a cotton hybrid having the plant of claim 2 as a parent until an advanced generation is attained, said advanced generation being $F_5$ or greater.

23. The process of claim 22, in which inbreeding includes self-pollination.

* * * * *